United States Patent [19]
Baker

[11] Patent Number: 5,863,288
[45] Date of Patent: Jan. 26, 1999

[54] OVERLAPPED-STYLE ABSORBENT CORE STRUCTURE COMPRISING MULTIPLE STORAGE AND ACQUISITION CELLS

[75] Inventor: Andrew T. Baker, Kent, Wash.

[73] Assignee: Paragon Trade Brands, Inc., Lawrenceville, Ga.

[21] Appl. No.: 536,659

[22] Filed: Sep. 29, 1995

[51] Int. Cl.$^6$ ............................. A61F 13/15; A61F 13/20
[52] U.S. Cl. ...................... 604/378; 604/385.1; 156/276
[58] Field of Search ................... 604/368, 367, 604/378, 380, 385.1; 156/276, 292, 308.4, 291

[56] References Cited

U.S. PATENT DOCUMENTS

| | | |
|---|---|---|
| Re. 32,957 | 6/1989 | Elias . |
| 4,235,237 | 11/1980 | Mesek et al. . |
| 4,333,462 | 6/1982 | Holtman et al. . |
| 4,333,463 | 6/1982 | Holtman . |
| 4,551,191 | 11/1985 | Kock et al. ............................. 156/276 |
| 4,560,372 | 12/1985 | Pieniak . |
| 4,578,068 | 3/1986 | Kramer et al. . |
| 4,600,458 | 7/1986 | Kramer et al. ........................ 156/276 |
| 4,715,918 | 12/1987 | Lang ...................................... 156/276 |
| 4,834,735 | 5/1989 | Alemany et al. . |
| 4,851,069 | 7/1989 | Packard et al. ........................ 156/276 |
| 4,935,022 | 6/1990 | Lash et al. . |
| 4,960,477 | 10/1990 | Mesek . |
| 4,988,344 | 1/1991 | Reising et al. . |
| 4,988,345 | 1/1991 | Reising . |
| 5,021,050 | 6/1991 | Iskra . |
| 5,047,023 | 9/1991 | Berg . |
| 5,061,259 | 10/1991 | Goldman et al. . |
| 5,098,423 | 3/1992 | Pieniak et al. . |
| 5,141,794 | 8/1992 | Arroyo . |
| 5,147,343 | 9/1992 | Kellenberger . |
| 5,149,335 | 9/1992 | Kellenberger et al. . |
| 5,156,902 | 10/1992 | Pieper et al. . |
| 5,248,524 | 9/1993 | Soderlund . |
| 5,260,345 | 11/1993 | DesMarais et al. . |
| 5,281,207 | 1/1994 | Chmielewski et al. . |
| 5,314,738 | 5/1994 | Ichikawa . |
| 5,354,290 | 10/1994 | Gross . |
| 5,356,403 | 10/1994 | Faulks et al. . |
| 5,364,686 | 11/1994 | Disselbeck et al. . |
| 5,411,497 | 5/1995 | Tanzer et al. . |
| 5,415,717 | 5/1995 | Perneborn ........................... 156/276 |

FOREIGN PATENT DOCUMENTS 77 00037  9/1978  France .

*Primary Examiner*—John G. Weiss
*Assistant Examiner*—Ki Yong O
*Attorney, Agent, or Firm*—Klarquist Sparkman Campbell Leigh & Whinston, LLP

[57] ABSTRACT

The present invention provides an absorbent core structure comprising storage cells and acquisition cells that is useful, for example, for disposable absorbent garments. Within the storage cells of the absorbent core structure is disposed a quantity of superabsorbent material. The acquisition cells are devoid of superabsorbent material or other materials that would impede the movement of liquid therethrough and are preferably open. The acquisition cells can thus function as channels that allow liquids to be freely distributed within the absorbent core structure by mass flow and/or capillary action, thus helping to prevent gel blocking.

52 Claims, 3 Drawing Sheets

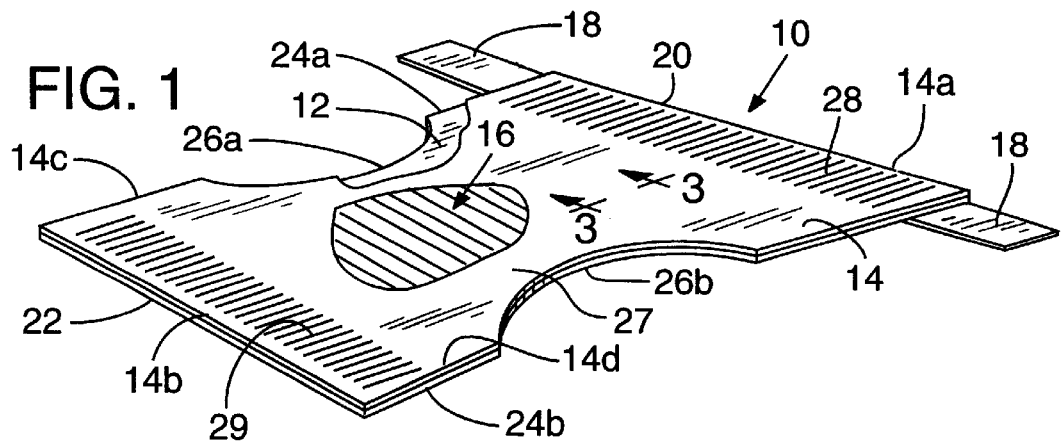
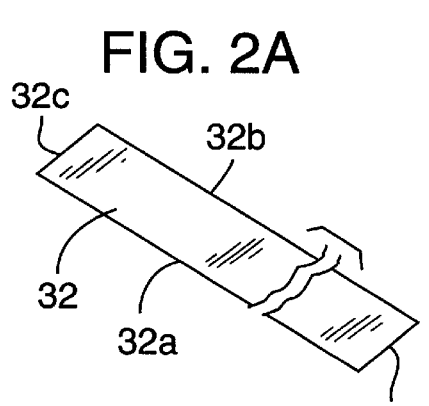
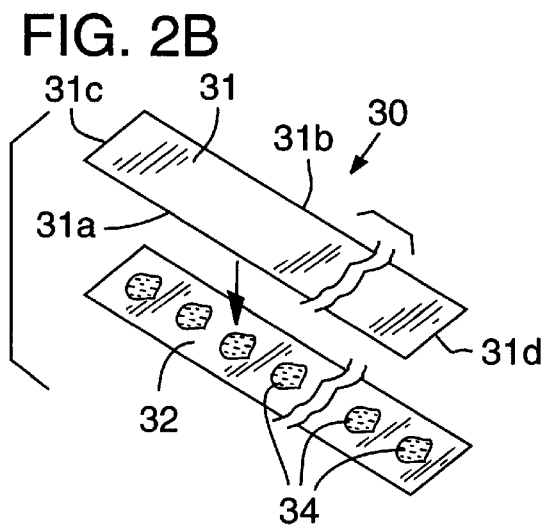
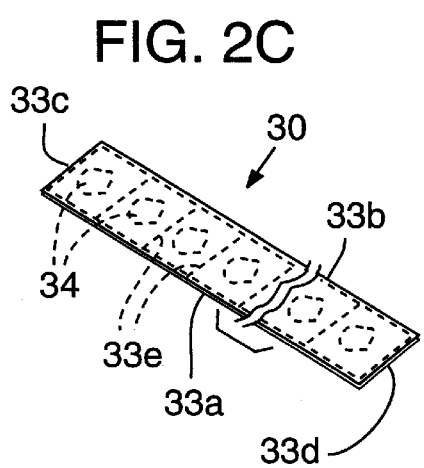
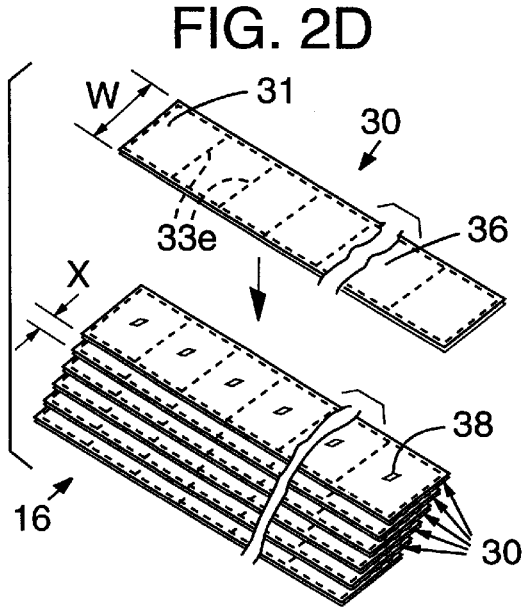

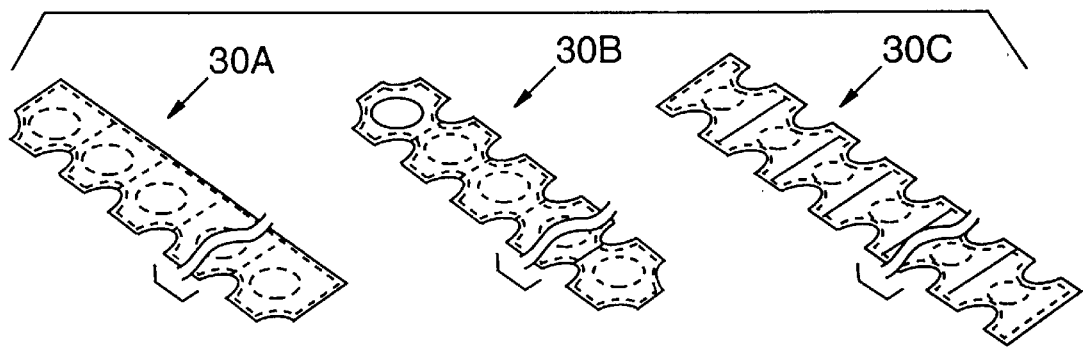
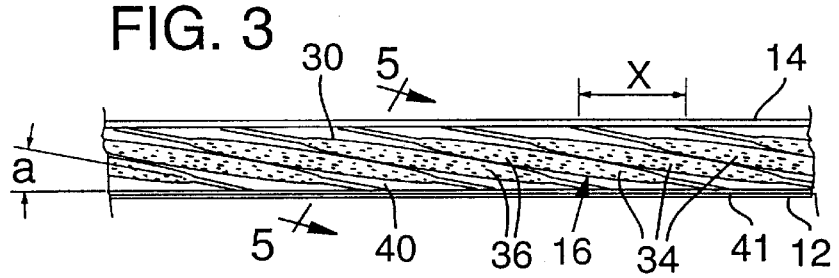
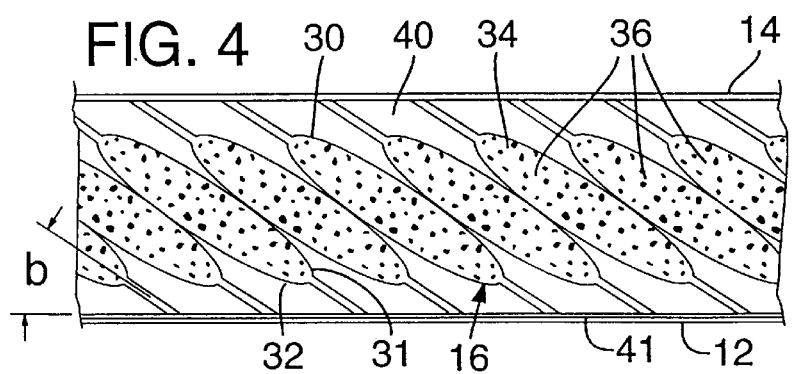

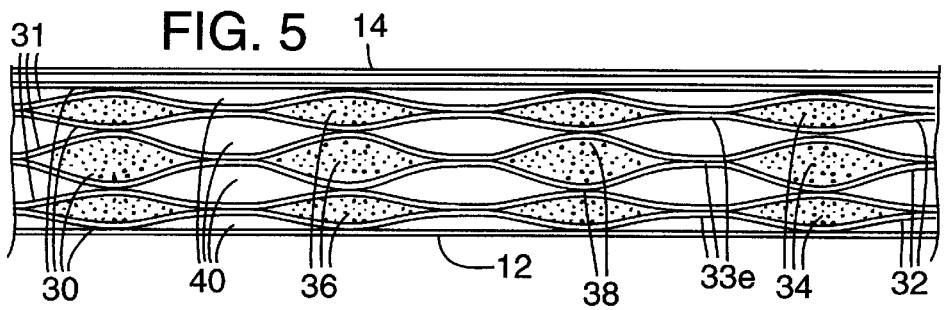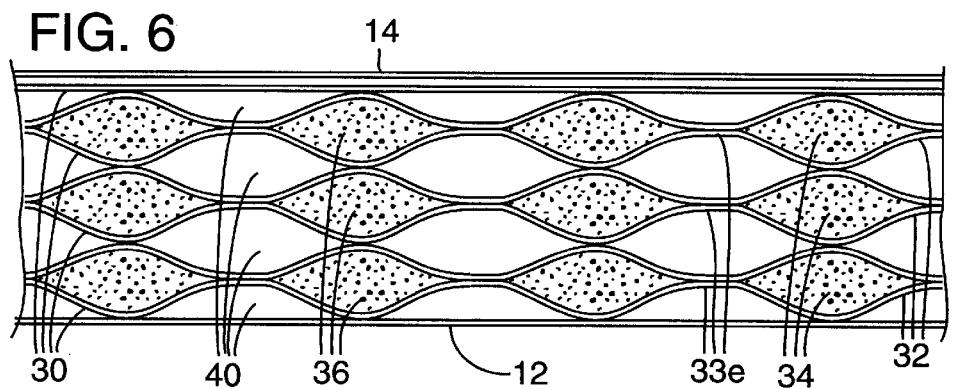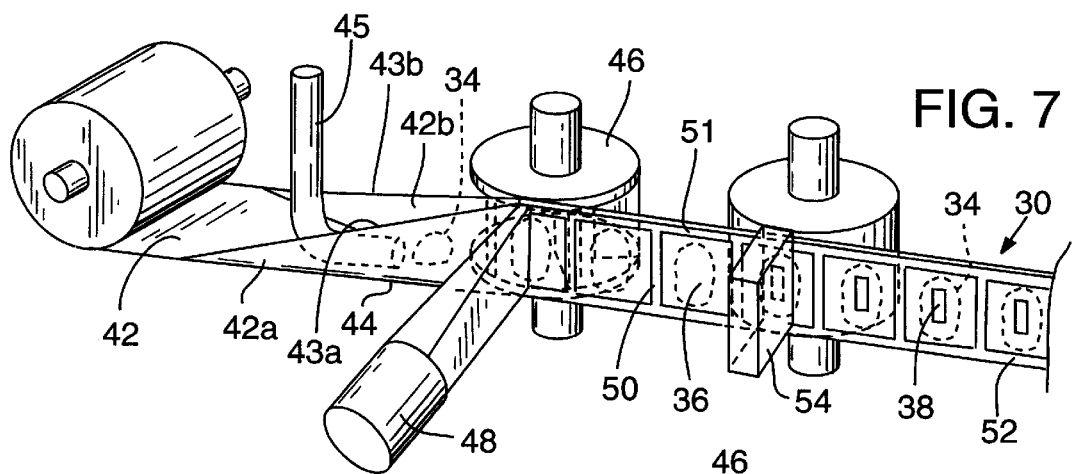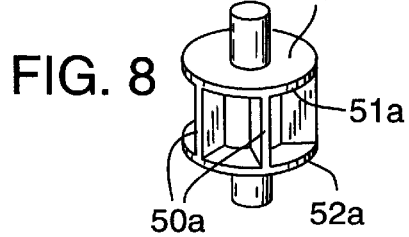

OVERLAPPED-STYLE ABSORBENT CORE STRUCTURE COMPRISING MULTIPLE STORAGE AND ACQUISITION CELLS

FIELD OF THE INVENTION

The present invention relates generally to an absorbent core structure for a disposable absorbent garment. More particularly, the present invention provides an absorbent core structure comprising a plurality of overlapping storage cells and acquisition cells in a shingle-style configuration.

BACKGROUND OF THE INVENTION

Traditionally, disposable absorbent garments, such as infant diapers or training pants, adult incontinence briefs and other such products are constructed with a moisture-impervious outer or backing sheet, a moisture-pervious body-contacting inner liner sheet, and a moisture-absorbent core sandwiched and encased between the liner and backing sheets.

Much effort has been expended to find cost-effective materials for absorbent cores that display good liquid absorbency and retention. Superabsorbent materials in the form of granules, beads, fibers, etc., have been favored for such purposes. Such superabsorbent materials are generally polymeric gelling materials that are capable of absorbing large quantities of liquids such as water and body wastes relative to their weight and of retaining such absorbed materials even under moderate pressure.

The ability of a superabsorbent material to absorb liquid is dependent upon the form, position, and/or manner in which particles of the superabsorbent are incorporated into the absorbent core. Whenever a particle of the superabsorbent material in an absorbent core is wetted, it swells and forms a gel. Gel formation can block liquid transmission into the interior of the absorbent core, a phenomenon called "gel blocking." Gel blocking in and adjacent a zone in an absorbent core of initial liquid contact prevents liquid from rapidly diffusing or wicking past the "blocking" particles of superabsorbent into the rest of the absorbent core; further imbibition of liquid by the absorbent core must then take place via a diffusion process that can be much slower than the rate at which liquid is applied to the core. Gel blocking can thus result in leakage from the absorbent article well before the absorbent core is fully saturated.

Efficient imbibition of liquid by the absorbent core at the point of initial liquid contact and rapid distribution of the liquid away from this point is necessary to insure that the absorbent core has sufficient capacity to absorb subsequently deposited liquids. What is needed is an absorbent core that quickly imbibes and distributes large quantities of liquids throughout the core while minimizing gel blocking during initial liquid contact.

Preferably, the absorbent core is also thin in order to improve the appearance of a garment with such an absorbent core and the comfort of the wearer of the garment. The importance of thin, comfortable garments is disclosed, for example, in U.S. Pat. No. 5,098,423 (Pieniak et al.), which is incorporated herein by reference.

SUMMARY OF THE INVENTION

One object of the present invention is to provide a thin, highly absorbent core structure useful, for example, for disposable absorbent garments. To that end, the present invention provides a multi-layered absorbent core structure, adjacent absorbent layers of which are offset so as to partially overlap one another to produce a configuration resembling shingles on a roof, i.e., a "shingle-like configuration."

The absorbent core structure comprises a plurality of "storage cells" and "acquisition cells." A quantity of absorbent and/or superabsorbent material is disposed within the discrete storage cells. The acquisition cells, by contrast, are devoid of material that would impede liquid movement therethrough and preferably are empty. The acquisition cells function as channels to distribute liquids throughout the absorbent-core structure, thereby overcoming the problem of gel blocking and promoting rapid liquid transfer throughout the absorbent core structure.

In order to produce a layer of the absorbent core structure according to one embodiment of the invention, discrete quantities of an absorbent and/or superabsorbent material are deposited at spaced locations between liquid-pervious strips or sheets (or between facing halves of a pleated or folded double-width strip or sheet or by any other arrangement that provides at least two facing surfaces wherein absorbent or superabsorbent material can be contained therebetween). The sheets are then bonded or attached to each other along open edges and at spaced locations by any conventional adhesive or other bonding means, e.g., sonic bonding. Each layer thereby comprises a plurality of discrete storage cells, with a quantity of the absorbent and/or superabsorbent material captured in each of the storage cells.

In order to produce an absorbent core structure according to one embodiment of the invention, absorbent layers are disposed contiguously relative to each other in a partially overlapping configuration such that the longitudinal edges of adjacent absorbent layers are offset, preferably by a distance less than one-half the width of the layer. Preferably, the absorbent layers are all the same size. A liquid-permeable sheet may optionally be interposed between adjacent absorbent layers.

Adjacent absorbent layers can be attached to each other by any conventional adhesive or bonding means, e.g., by adhesive applied to the exterior of each of the layers (except the topmost layer) at spaced locations, e.g., approximately at the mid-region of each of the storage cells in the layers.

Acquisition cells are formed between and bounded by adjacent absorbent layers. Additional acquisition cells or spaces or openings may also be provided in the layers of the absorbent core structure to facilitate liquid transfer throughout the absorbent core structure.

Another object of the present invention is to provide a wide variety of disposable absorbent garments incorporating an absorbent core structure according to the invention. In one embodiment, the garment comprises a moisture-impervious backing sheet and a moisture-pervious liner sheet. The absorbent core is positioned between the liner layer and backing layer. In such a garment, when dry, the individual layers of the absorbent core structure lie down relatively flat, i.e., at a low angle relative to the backing sheet. When the superabsorbent material in the storage cells absorbs liquid, the resulting swelling of the superabsorbent material causes the storage cells to swell (and, concomitantly, the acquisition cells between adjacent absorbent layers to increase in size). As a result, the angle of the layers of the absorbent core structure increases relative to the backing sheet.

These and other objects, features and advantages of the present invention will become apparent to those skilled in the art from the following description and drawings.

BRIEF DESCRIPTION OF THE DRAWINGS

FIG. 1 is an isometric view of an absorbent garment incorporating an absorbent core according to the invention, with portions of a liner sheet broken away to show the absorbent core.

FIGS. 2A–E are schematic views showing a method of manufacturing an absorbent layer and an absorbent core structure according to an embodiment of the invention. A–C: A method of manufacturing a single absorbent layer. D: A method of manufacturing an absorbent core structure from multiple absorbent layers. E: Three examples of an absorbent layer in which one (30A) or both longitudinal edges (30B and 30C) is scalloped.

FIG. 3 is an enlarged cross-sectional view of a portion of the absorbent garment shown in FIG. 1 taken along line 3—3.

FIG. 4 is a cross-sectional view of the absorbent garment shown in FIG. 3 after absorbing liquid.

FIG. 5 is an enlarged cross-sectional view of the absorbent garment shown in FIG. 3 taken along a line 5—5.

FIG. 6 is a cross-sectional view of the absorbent garment as shown in FIG. 5 after absorbing liquid.

FIG. 7 is a simplified isometric view of a method for manufacturing an absorbent layer of an absorbent core structure according to an embodiment of the invention.

FIG. 8 is an isometric view of a mandrel used for sonic bonding sheet material to produce an absorbent layer by the method shown in FIG. 7.

DETAILED DESCRIPTION OF PREFERRED EMBODIMENT

The present invention provides, inter alia, absorbent structures having both discrete storage cells and acquisition cells, useful, for example, for incorporation into disposable absorbent garments.

FIG. 1 illustrates an embodiment of a disposable absorbent garment 10, typically for use as a baby or infant diaper or as an adult incontinence brief. The absorbent garment 10 can also be sealed or joined along the opposed side edges 24a, 24b to form a conventional pull-on style training pant.

The garment 10 has a moisture-impervious outer (or backing) layer (or sheet) 12 and a moisture-pervious inner (or liner) layer (or sheet) 14. A moisture-absorbent core (or pad) 16, incorporating an absorbent core structure according to an embodiment of the invention, is disposed superposedly on at least a portion of backing sheet 12 so as to be sandwiched between the backing sheet 12 and liner sheet 14. The resulting trilaminar structure can be held together by any of various conventional means, e.g., adhesive or other bonding means (e.g., sonic bonding, embossing, needle punch, etc.).

The garment 10 has a first laterally extending waist edge 20 and a second waist edge 22 that are spaced so as to be situated along back and front waist regions, respectively, of a wearer of the garment. The garment 10 also has opposed first and second side edges, or margins, 24a, 24b, respectively.

The liner sheet 14 has opposed first and second waist edge regions 14a, 14b and side edges 14c, 14d that can be coextensive with the backing sheet 12 (as shown) or can terminate at some point inwardly from the edges of the backing sheet, as desired.

Such garments also typically include outer leg gathers or seals, stretchable waistbands, and tapes or other fasteners at the waist. A pair of tape fasteners are indicated generally at 18 extending outwardly from opposite side edges 24a, 24b adjacent first waist edge 20, which is usually situated on the back waist region of the wearer.

The side edges 24a, 24b have incut leg regions 26a, 26b adapted to fit about the legs of a wearer. The garment thus has a generally hourglass-shaped configuration so as to define a crotch region 27 located generally between the incut leg regions 26a, 26b. The crotch region 27 has a narrower width than the waist edges 20, 22.

Waist gathers 28, 29, are preferably provided adjacent the waist edges 20, 22, respectively. The waist gathers are preferably formed by incorporation of elastic material or the like adjacent the waist edges so as to form rugosities in the waist edges. The waist gathers 28, 29 provide a more comfortable fit for the wearer.

The absorbent core, or pad, 16, comprises an absorbent core structure according to an embodiment of the invention as described in detail below. The absorbent core 16 is generally disposed in the crotch region 27. The absorbent core 16 may have a rectangular shape or any other suitable shape such as an hourglass configuration.

Due to the wide variety of backing and liner sheet constructions and materials currently available, the invention is not intended to be limited to any specific materials or constructions of these components. The backing sheet 12 is of any suitable pliable liquid-impervious material known in the art. Typical backing sheet materials include films of polyethylene, polypropylene, polyester, nylon, and polyvinyl chloride and blends of these materials. For example, the backing sheet can be of a pigmented polyethylene film having a thickness in the range of 0.02–0.04 mm. The moisture-pervious liner sheet 14 can be of any suitable relatively liquid-pervious material known in the art that permits passage of liquid therethrough. Nonwoven liner sheet materials are exemplary because such materials readily allow the passage of liquids to the underlying absorbent core 16. Examples of suitable liner sheet materials include nonwoven webs of nylon, polyester, and polypropylene fibers and blends of these materials. Suitable commercially available liner sheet materials include Cerex® (James River Corporation), Reemay® (Intertec Corporation), and Sonterra® (Dupont Corporation). The liner sheet can comprise multiple layers. See, e.g., U.S. Pat. No. 5,188,624 (Young, Sr., et al.), incorporated herein by reference, for additional information regarding materials and manufacture of absorbent garments.

Those skilled in the art will appreciate that the absorbent garments of the present invention may incorporate a wide variety of additional elements conventionally used in absorbent garments (e.g., additional liner sheets, layers of natural or synthetic fibers, etc.) and that the elements provided herein can be altered or adapted by conventional means.

For example, a suitable liner sheet may be placed between the absorbent core and the liquid-impervious backing sheet to facilitate free liquid transport within the absorbent core. One may also place a layer of comminuted wood (fluff) pulp or a mixture of natural or synthetic fibers (preferably a thin layer) between the absorbent core and the liquid-impervious backing sheet to give the absorbent garment a softer feel and to assist in containment of free liquid. Additionally, a liner sheet or compacted fiber layer may be placed around the outer margins of the absorbent core.

Absorbent core structures according to the invention also are useful for a wide variety of other absorbent garments and related uses, including, but not limited to, adult incontinence garments, sanitary napkins, disposable panties, children's training pants, bed pads, and the like.

In general, each absorbent layer 30 of the absorbent core structure 16 is produced by capturing a quantity of absorbent and/or superabsorbent material at spaced locations between at least two facing surfaces of liquid-pervious strips or sheets, wherein the facing surfaces are provided by two opposed strips or sheets, or by facing surfaces of a single pleated or folded strip or sheet, or by any other arrangement that provides at least two facing surfaces between which an absorbent and/or superabsorbent material can be captured.

FIGS. 2A–D together show a preferred method of manufacturing an absorbent layer 30 and an absorbent core structure 16 according to an embodiment of the invention, the absorbent core structure 16 comprising multiple absorbent layers 30 layer in an offset, partially overlapping shingle-style configuration as shown.

As shown in FIG. 2B, an absorbent layer 30 of the absorbent core structure 16 preferably comprises two opposed strips 31, 32 of a non-woven liquid-pervious sheet material. (The strip 32 is shown in FIG. 2A.) The strips 31, 32 as shown have identical size and shape. The strips 31, 32 each have opposed first and second longitudinal edges, or margins, 31a, 31b, and 32a, 32b, respectively, and opposed first and second end edges 31c, 31d, and 32c, 32d, respectively. On the strip 32 is deposited discrete quantities of a liquid-absorbent material 34 (FIG. 2B), preferably a superabsorbent material (or, if desired, a mixture of a superabsorbent material with another material, e.g., another liquid-absorbent or fibrous material) at spaced locations. The two strips 31, 32 are bonded, sealed, or otherwise attached to each other substantially superposedly by any conventional means to create inter-strip bonds along each of their combined longitudinal edges 33a, 33b and end edges 33c, 33d and between each location of superabsorbent material 33e (see FIG. 2C). As shown in FIG. 2D, the bonds thus define multiple storage cells 36 in each absorbent layer 30, each cell 36 containing a quantity of the superabsorbent material 34.

The length and or width of each of the strips 31, 32 need not be the same. In fact, in some embodiments of the invention, it may be desirable to locate a shorter or narrower strip centrally along the surface of a longer or wider strip, leaving free ends 32c and/or 32d, or edges, 32a and/or 32b, or both. The free ends or edges can then be fastened to other parts of an absorbent garment incorporating the absorbent core structure, e.g., to the liner sheet 14 or the backing sheet 12.

In addition, although the first and second longitudinal edges 31a, 31b, and 32a, 32b and end edges 31c, 31d and 32c, 32d of strips 31 and 32, respectively, are shown in FIG. 2A as being straight, these edges may have any shape or conformation, e.g., scalloped, fringed or digitated, etc. For example, scalloping one or more edges, e.g., as shown in FIG. 2E, may facilitate the movement of free liquid throughout the absorbent core structure.

The storage cells 36 thus formed can be generally square or rectangular in shape (FIGS. 2C–2D), each storage cell being analogous to a ravioli having a partial "filling" of superabsorbent material. Each storage cell 36 is discrete, i.e., the contents of each storage cell are separated from the contents of all other storage cells and from the contents, if any, of acquisition cells 40 (described below), even though storage and acquisition cells are in liquid contact with each other.

As shown in FIGS. 2C and 2D, each absorbent layer 30 consists of a row or linear array of multiple storage cells 36. Alternatively, each absorbent layer 30 can comprise a two-dimensional pattern, e.g., multiple rows, of storage cells. In order to produce an absorbent layer having such a two-dimensional pattern storage cells, a method analogous to that shown in FIGS. 2A and 2B can be used, for example. Opposed strips 31, 32 are replaced by first and second sheets of a similar liquid-pervious material, each sheet preferably having the same shape and dimensions, e.g., a square, rectangular, hourglass, or other shape. Superabsorbent material is deposited on the second sheet in a two-dimensional pattern, which may be either regular or irregular. The two sheets are bonded, sealed, or otherwise attached to each other by any conventional means to create bonds along each of their combined edges and between each location of superabsorbent material so as to define multiple fully-enclosed storage cells in each absorbent layer, each cell having captured within it a quantity of superabsorbent material. In order to attach adjacent absorbent layers together to form a multi-layered absorbent structure according to the invention, glue spots or stripes 38 can be positioned approximately central to, or in the mid-region of, all or selected storage cells.

As an additional alternative, superabsorbent material can be disposed in preformed pockets in a liquid-pervious sheet. A second liquid-pervious sheet, e.g., a flat sheet, can then be attached to the second sheet, capturing the superabsorbent material in the pockets.

As a further alternative, superabsorbent material can be introduced into preformed cells produced, by the attachment of facing strips or sheets to each other. The cells containing the superabsorbent material can then be sealed to produce discrete storage cells. Some preformed cells can remain free of superabsorbent material.

Those skilled in the art will appreciate that absorbent core structures may combine absorbent layers according to the present invention with conventional liquid-absorbent or non-absorbent material in various ways. For example, an absorbent core may comprise absorbent layers according to the present invention alternating with layers of a conventional liquid-absorbent material such as fluff pulp. Alternatively, an absorbent core may combine regions comprising absorbent layers according to the present invention with regions consisting of conventional materials such as conventional fluff pulp. For example, an absorbent core may comprise (1) a discrete panel comprising overlapping absorbent layers according to the present invention positioned towards front and central areas of an absorbent garment and (2) conventional fluff pulp in the remaining areas of the absorbent core.

The liquid-pervious sheets 31, 32 from which absorbent layers 30 are manufactured can, for example, be non-woven webs of carded polyester fibers with a latex binder, spun-bonded continuous polypropylene fibers thermally bonded together, cellulosic pulp fibers, or other appropriate materials known in the art.

The quantity of superabsorbent material 34 in each storage cell 36 preferably only partially fills each storage cell so as to allow room for swelling of the superabsorbent material upon fluid absorption without rupturing the storage cell.

The superabsorbent material 34 can be any suitable particulate (e.g., flaked, particulate, granular, or powdered) or fibrous material known in the art that has the ability to absorb large quantities of liquids, including body fluids, preferably in excess of 30 to 40 parts of liquid per part thereof. Superabsorbent materials generally fall into three classes: starch graft copolymers, cross-linked carboxymethylcellulose derivatives, and modified hydrophilic polyacrylates. Exemplary superabsorbent materials include, but are not limited to: carboxylated cellulose, hydrolyzed acrylonitrile-grafted starch, acrylic acid derivative polymers, polyacrylonitrile derivatives, polyacrylamide-type compounds, and saponified vinyl acetate/methyl acrylate copolymers. Specific examples of commercially available superabsorbent materials are "Sanwet" (supplied by Sanyo Kasei Kogyo Kabushiki Kaisha) and "Sumika Gel" (supplied by Sumitomo Kagaku Kabushiki Kaisha).

The superabsorbent material can be mixed with other materials known in the art, preferably fibrous materials, to form a liquid-absorbent matrix. These additional materials include, but are not limited to, hydrophilic fibrous materials such as cellulose fibers, modified cellulose fibers (e.g., comminuted wood pulp or internally cross-linked cellulose fibers), rayon, polyester fibers such as polyethylene terephthalate (DACRON™), hydrophilic nylon (HYDROFIL™), and hydrophilized hydrophobic fibers (e.g., surfactant- or silica-treated thermoplastic fibers derived, for example, from polyolefins).

As shown in FIG. 2D, an absorbent core structure according to an embodiment of the invention can be produced by disposing multiple absorbent layers 30 laterally adjacent to and in contact with each other such that the end edges 33c, 33d of adjacent absorbent layers are aligned and the longitudinal edges 33a, 33b are offset (in FIGS. 2D and 3, the distance by which the longitudinal edges are offset is shown as distance "x"), preferably by a distance less than one-half the width of the layer ("w" in FIG. 2D). The absorbent core structure so produced has a partially overlapping configuration similar in appearance to shingles on a roof. The layers are attached to each other by any conventional means, e.g., adhesive or bonding means (e.g., sonic bonding, embossing, needle punch etc.). For example, as shown in FIGS. 2D and 7, a spot (or line or stripe) of adhesive 38 can be applied to each of the layers (excepting, perhaps, the outermost layer or layers) at spaced locations, e.g., to one exterior surface of each layer 30 at a point approximately central, or in the mid-region of, each of the storage cells 36.

As shown in FIG. 3, each absorbent layer 30 can consist of a single row, or linear array, of multiple storage cells 36. Alternatively, each absorbent layer 30 can consist of multiple rows of storage cells 36. Such absorbent layers having multiple rows of storage cells can be attached to each other, for example, with glue spots or stripes 38 positioned approximately central to, or in the mid-region of, each storage cell 36, in order to produce a multi-layered absorbent core structure.

FIG. 3 shows a cross-section of absorbent core structure 16 sandwiched between a liquid-impervious backing sheet 12 and a liquid-pervious liner sheet 14. The plane of the absorbent core structure is substantially parallel to that of the backing sheet 12 and liner sheet 14. The absorbent layers 30 lie down relatively flat, i.e., are disposed at a low angle (acute angle "a" as shown) relative to the backing sheet 12 and liner sheet 14 and to the plane of the absorbent core structure 16, preferably an angle less than about 30 degrees, more preferably less than about 15 degrees.

As shown in FIG. 4, as superabsorbent material 34 in the storage cells 36 absorbs liquid and swells, the storage cells 36 expand. Expansion of the storage cells 36 may cause the angle of the absorbent layers to increase relative to the backing and liner sheets; i.e., the absorbent layers may "stand up" (compare angle "b" of FIG. 4 to angle "a" of FIG. 3).

FIGS. 5 and 6 show acquisition cells 40 formed between the absorbent layers 30 of the absorbent core structure 16. The acquisition cells are devoid of superabsorbent material or other materials that would impede the movement of liquid therethrough and are preferably open (i.e., empty) to permit mass flow of free liquids therethrough and to make the absorbent core structure as thin as possible. The absorbent core structure can also be fabricated such that the acquisition cells contain liquid-absorbent or non-absorbent materials known in the art that would produce minimal impedance to the movement of liquid through the acquisition cells. For example, an appropriate material can be (1) disposed between adjacent absorbent layers as a continuous sheet or array or (2) deposited, injected, or otherwise disposed in spaced locations. Depending upon the material disposed between absorbent layers and whether it is continuous or discontinuous, adjacent absorbent layers separated by such a material can be attached to each other or to the interposed material.

Liquid can move in acquisition cells 40 by mass flow or by capillary action, e.g., in the sheet material 31, 32 of the absorbent layers bounding each acquisition cell 40. The acquisition cells 40 can therefore function as fluid channels that allow fluids to be distributed within the absorbent core structure. The acquisition cells 40 thus help to prevent "gel blocking" and ensure that liquid is quickly carried away from the point of deposition, i.e., away from the skin of the wearer of an absorbent garment incorporating an absorbent core according to the present invention.

As shown most clearly in FIG. 6, expansion of the storage cells 36 upon liquid absorption causes the acquisition cells 40 to also expand, thereby facilitating fluid delivery throughout the absorbent core structure.

The acquisition cells 40 preferably contain no materials when dry as to allow the absorbent core structure to be made as thin as possible. If desired, some or all of the acquisition cells can contain a liquid-absorbent or non-absorbent material known in the art that would produce minimal impedance to liquid movement through the acquisition cells. Optionally, holes or spaces can also be provided in the absorbent core structure to further facilitate fluid transfer by mass flow. To assist in liquid transfer throughout the absorbent core structure, the structure may comprise one or more wicking layers 41 in liquid contact with the open end of the acquisition cells, e.g., disposed between the absorbent core structure 16 and the backing sheet 12. The wicking layer is preferably composed of a conventional hydrophilic woven sheet material.

An alternate method of making an absorbent layer for an absorbent core structure according to the present invention is shown in FIG. 7. Instead of employing two separate strips 31, 32 as shown in FIG. 2, a single double-width strip 42 of liquid-pervious material is folded lengthwise to produce facing halves 42a, 42b. Each of the facing halves 42a, 42b has an open longitudinal edge 43a, 43b, respectively. The two facing halves 42a, 42b share a longitudinal closed edge at the fold 44. Discrete quantities of superabsorbent material 34 are deposited at spaced locations between the facing halves 42a, 42b by a superabsorbent injector 45. The facing halves 42a, 42b are then attached together at spaced locations by sonic bonding to form bonds 50, 51 between the locations of the superabsorbent material 34 and along the open edge 43a, 43b of the folded sheet-like material, respectively, thereby producing storage cells 36. (optionally, a bond 52 can also be formed along the fold 44.) The spacing and width of the bonds 50, 52 thus formed are defined by edges 50a, 51a (and, if there is a bond 52 along the fold 44, edge 52a) of a rotatable mandrel 46. The mandrel 46 is used to direct and focus ultrasonic energy produced by an ultrasonic transducer (not shown) onto a defined area of the facing halves 42a, 42b, causing them to be sonically bonded together to form bonds 50, 51 (and, if present, 52). (The mandrel 46 alone is shown in FIG. 8.) After sonic bonding, an adhesive applicator 54 applies a spot (or stripe or line) of adhesive 38 on an outer surface of the absorbent layer 30, e.g., at an external location approximately central to, or in the mid-region of, each of the storage cells 36, as shown. The elongate absorbent layer thus produced is finally cut to the desired length (not shown) and layered as described above to produce an absorbent core structure.

In an absorbent core structure according to the present invention, storage cells can alternate with acquisition cells, i.e., the ratio of the number of storage cells to acquisition cells can be approximately 1:1, as shown for example in FIGS. 5 and 6. However, this ratio can be varied. Those of ordinary skill in the art will appreciate that the storage and acquisition cells can have a variety of regular or irregular shapes, sizes, and configurations. Each absorbent layer 30 can comprise a number of differently shaped storage cells, and different layers of a multi-layer absorbent core can have similar or dissimilar patterns of storage cells. The shapes and sizes of the storage cells 36 can be varied, for example, by varying the configuration, spacing, and width of the bonds 33e by which facing strips of sheet material 32 in each layer 30 are attached to each other. Similarly, the size and shape of the acquisition cells 40 can be varied by, for example, varying (1) the manner in which adjacent absorbent layers of the absorbent core structure are attached to each other and (2) the orientation of each absorbent layer in the structure with respect to adjacent absorbent layers.

Absorbent core structures as described above can also be stacked or layered to form a thicker, more absorbent structure, e.g., with liquid-pervious sheets optionally separating adjacent layers.

Having illustrated and described the invention generally with respect to preferred embodiments, it should be apparent to those skilled in the art that modifications are possible without departing from the spirit of the invention.

What is claimed is:

1. An absorbent article comprising:
   a liquid-impervious backing sheet;
   a liquid-pervious liner sheet; and
   an absorbent core between the liner sheet and the backing sheet, the absorbent core comprising a plurality of liquid-absorbent layers, each layer having an edge and comprising facing liquid-pervious sheet portions attached together and containing a liquid-absorbent material, and each layer attached to another layer with respective edges of the layers offset such that the layers are in a partially overlapping shingle-like configuration.

2. The absorbent article of claim 1 wherein the facing sheet portions of each layer are attached together to define a plurality of discrete storage cells containing the liquid-absorbent material.

3. The absorbent article of claim 2 wherein the liquid-absorbent material comprises a superabsorbent material.

4. The absorbent article of claim 2 wherein each layer comprises a linear array of the storage cells.

5. The absorbent article of claim 2 wherein storage cells alternate with acquisition cells that are devoid of material that would impede liquid movement therethrough.

6. The absorbent article of claim 1 further comprising at least one acquisition cell between the layers that is devoid of material that would impede liquid movement therethrough.

7. The absorbent article of claim 6 wherein said at least one acquisition cell is empty.

8. The absorbent article of claim 1 wherein each layer is attached to another layer at spaced locations.

9. The absorbent article of claim 2 wherein each layer is attached to another layer approximately at midregions of the storage cells.

10. The absorbent article of claim 1 wherein the facing liquid-pervious sheet portions are facing half-sheets produced by folding a liquid-pervious sheet longitudinally, thereby producing the facing half-sheets on opposite sides of a fold.

11. The absorbent article of claim 12 wherein each of the absorbent layers comprises the fold, a longitudinal edge spaced apart from the fold, and spaced end edges, and the half-sheets are attached together at least along the longitudinal edge and along the end edges.

12. The absorbent article of claim 2 wherein the liquid-absorbent material is disposed between the facing sheet portions at spaced locations and the facing sheet portions are attached together between the locations of the liquid-absorbent material to define the storage cells.

13. The absorbent article of claim 11 wherein the liquid-absorbent material is disposed between the facing half-sheets at spaced locations and the facing half-sheets are attached together between the locations of the liquid-absorbent material to define a plurality of discrete storage cells containing the liquid-absorbent material.

14. The absorbent article of claim 1 wherein the facing first and second liquid-pervious sheet portions are facing first and second liquid-pervious sheets or strips.

15. The absorbent article of claim 14 wherein the liquid-absorbent material is disposed between the facing sheets or strips at spaced locations and the sheets or strips are attached together between the locations of the liquid-absorbent material to define a plurality of discrete storage cells containing the liquid-absorbent material.

16. The absorbent article of claim 1 wherein the absorbent core structure defines a plane and the liquid-absorbent layers are disposed at a first angle relative to the plane prior to liquid absorption by the liquid-absorbent layers and at a second angle relative to the plane after liquid absorption by the layers, the second angle being greater than the first angle.

17. The absorbent article of claim 16 wherein the first angle is less than about 30 degrees.

18. The absorbent article according to claim 1 wherein each layer has spaced first and second longitudinal edges and spaced first and second end edges and respective first and second end edges of the layers are aligned and respective first and second longitudinal edges of the layers are offset.

19. The absorbent article of claim 1 wherein the layers are of substantially the same size.

20. The absorbent article of claim 5 wherein said at least one acquisition cell expands upon liquid absorption by the layers.

21. An absorbent core structure comprising (a) a plurality of partially overlapping liquid-absorbent layers of substantially the same size, each layer having an edge and comprising facing liquid-pervious sheet portions attached together to define a plurality of discrete storage cells containing a liquid-absorbent material, and each layer being attached to another layer with respective edges of the layers offset in a shingle-like configuration; and (b) at least one acquisition cell between the layers that is devoid of material that would impede liquid movement therethrough.

22. The absorbent core structure of claim 21 comprising a plurality of the acquisition cells.

23. A disposable absorbent garment comprising:
a liquid-impervious backing sheet;
a liquid-pervious liner sheet; and
an absorbent core between the liner sheet and the backing sheet comprising a plurality of partially overlapping absorbent layers, each layer having an edge and comprising facing liquid-pervious sheet portions attached together to contain a liquid-absorbent material, and each layer attached to another layer with respective edges of the layers offset in a shingle-like configuration.

24. The absorbent garment of claim 23 further comprising a wicking layer in fluid contact with the absorbent core.

25. The absorbent garment of claim 23 wherein the absorbent layers are disposed at an angle of less than about 30 degrees relative to the backing sheet when the absorbent core is dry.

26. The absorbent garment of claim 25 wherein the angle at which the absorbent layers are disposed relative to the backing sheet increases as a result of liquid absorption by the absorbent core.

27. A method of making an absorbent article comprising the steps of:
(a) disposing a liquid-absorbent material between facing liquid-pervious sheet portions;
(b) attaching the facing sheet portions together to contain the liquid-absorbent material, thereby producing a first liquid-absorbent layer having spaced-apart first and second edges;
(c) repeating steps (a) and (b) to produce a second liquid-absorbent layer having spaced-apart first and second edges;
(d) attaching the first layer to the second layer such that respective first and second edges of the first and second layers are offset such that the layers are in a partially overlapping shingle-like configuration, thereby producing an absorbent core; and
(e) disposing the absorbent core between a liquid-impervious backing sheet and a liquid-pervious liner sheet, thereby producing the absorbent article.

28. The method of claim 27 wherein the step of attaching the facing sheet portions together produces a first liquid-absorbent layer comprising a plurality of discrete storage cells, each storage cell containing the liquid-absorbent material.

29. The method of claim 27 wherein the liquid-absorbent material is a superabsorbent material.

30. The method of claim 27 wherein the facing liquid-pervious sheet portions are facing half-sheets, the method further comprising the steps of:
providing a liquid-pervious sheet; and
folding the liquid-pervious sheet to produce the facing half-sheets;
depositing quantities of a superabsorbent material at spaced locations between the half-sheets; and
attaching the facing half-sheets.

31. The method of claim 21 wherein the facing liquid-pervious sheet portions are facing liquid-pervious sheets or strips.

32. The method of claim 27 wherein the step of attaching the facing sheet portions further comprises the steps of:
attaching the facing sheet portions together to define spaced pockets;
depositing quantities of the liquid-absorbent material in selected pockets; and
sealing the selected pockets to produce discrete storage cells containing the liquid-absorbent material, thereby producing the first liquid-absorbent layer.

33. The method of claim 32 wherein some pockets are free of superabsorbent material.

34. The method of claim 27 comprising the step of attaching the first layer to the second layer at spaced locations.

35. The method of claim 27 wherein the step of attaching the first layer to the second layer thereby defines an acquisition cell between the first and second layers that is devoid of material that would impede liquid movement therethrough.

36. The method of claim 34 wherein the step of attaching the first layer to the second layer comprises applying an adhesive to an exterior surface of at least one of the layers.

37. The method of claim 36 wherein the step of attaching the first layer to the second layer comprises applying the adhesive at spaced locations on an exterior surface of at least one of the layers.

38. The method of claim 28 wherein the step of attaching the first layer to the second layer comprises applying the adhesive to an exterior surface of at least one of the layers at midregions of storage cells.

39. A method of producing a disposable absorbent garment comprising:
providing first and second liquid-absorbent layers, each layer having spaced-apart first and second edges and comprising facing liquid-absorbent sheets attached together and containing a liquid-absorbent material;
disposing the first layer adjacent the second layer such that the first and second layers are in a partially overlapping shingle-like configuration, with respective first edges of the layers being offset;
attaching the first layer to the second layer to define an acquisition cell between the first and second layers that is devoid of material that would impede liquid movement therethrough, thereby producing an absorbent core; and
disposing the absorbent core between a liquid-impervious backing sheet and a liquid-pervious liner sheet, thereby producing a disposable absorbent garment.

40. An absorbent article comprising a liquid-impervious backing sheet, a liquid-pervious liner sheet, and, disposed between the backing and liner sheets, an absorbent core that comprises a plurality of liquid-absorbent layers in a partially overlapping shingle-like configuration, each layer comprising facing liquid-pervious sheet portions attached together and containing a liquid-absorbent material and having spaced first and second longitudinal edges and spaced first and second end edges, wherein each layer is attached to another layer, respective first and second end edges of the layers are aligned, and respective first and second longitudinal edges of the layers are offset.

41. The absorbent article of claim 40 wherein the facing sheet portions are attached together to define a plurality of discrete storage cells containing the liquid-absorbent material.

42. The absorbent article of claim 41 further comprising at least one acquisition cell between layers that is devoid of a material that would substantially impede liquid movement therethrough.

43. The absorbent article of claim 42 wherein said at least one acquisition cell expands upon liquid absorption by the liquid-absorbent layers.

44. The absorbent article of claim 40 wherein the liquid-absorbent material comprises a superabsorbent material.

45. The absorbent article of claim 40 wherein the layers are disposed at a first angle relative to a plane defined by the absorbent core prior to liquid absorption by the layers and at a second angle relative to the plane after liquid absorption by the layers, wherein the second angle is greater than the first angle.

46. The absorbent article of claim 45 wherein the first angle is less than about 30 degrees.

47. The absorbent article of claim 40 wherein the layers are of substantially the same size.

48. An absorbent article comprising a liquid-impervious backing sheet, a liquid-pervious liner sheet, and, disposed between the backing and liner sheets, an absorbent core that comprises a plurality of liquid-absorbent layers, each layer comprising facing liquid-pervious sheet portions attached together to define a plurality of storage cells containing a superabsorbent material and having spaced first and second longitudinal edges and spaced first and second end edges, wherein each layer is attached to another layer to define at least one acquisition cell between layers that is devoid of material that would impede liquid movement therethrough, respective first and second end edges of the layers are aligned, and respective first and second longitudinal edges of the layers are offset such that the layers are in a partially overlapping shingle-like configuration.

49. The absorbent article of claim 48 wherein said at least one acquisition cell expands upon liquid absorption by the liquid-absorbent layers.

50. A method of making an absorbent article comprising the steps of:
(a) providing first and second liquid-absorbent layers, each layer comprising facing liquid-pervious sheet portions attached together to define a plurality of storage cells containing a superabsorbent material and having spaced first and second longitudinal edges and spaced first and second end edges;
(b) disposing the layers in a partially overlapping, shingle-like configuration such that respective first and second end edges of the layers are aligned and respective first and second longitudinal edges of the layers are offset;
(c) attaching the layers together such that at least one acquisition cell is defined between the layers that is devoid of material that impedes liquid movement therethrough. thereby producing an absorbent core; and
(e) disposing the absorbent core between a liquid-impervious backing sheet and a liquid-pervious liner sheet, thereby producing the absorbent article.

51. The method of claim 50 wherein said at least one acquisition cell expands upon liquid absorption by the layers.

52. The method of claim 50 wherein the step of attaching comprises attaching the layers together approximately at midregions of the storage cells.

* * * * *